US00PP30674P2

(12) United States Plant Patent
Pieters

(10) Patent No.: US PP30,674 P2
(45) Date of Patent: Jul. 9, 2019

(54) ***CHRYSANTHEMUM* PLANT NAMED 'G19FON04YE'**

(50) Latin Name: ***Chrysanthemum* X *morifolium***
Varietal Denomination: G19FON04YE

(71) Applicant: Elien Sofie Pieters, Oostnieuwkerke (BE)

(72) Inventor: Elien Sofie Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 0 days.

(21) Appl. No.: 15/732,910

(22) Filed: Jan. 13, 2018

(51) Int. Cl.
*A01H 5/02* (2018.01)

(52) U.S. Cl.
USPC ..... Plt./289

(58) Field of Classification Search
USPC ..... Plt./286, 289
See application file for complete search history.

*Primary Examiner* — Susan McCormick Ewoldt
(74) *Attorney, Agent, or Firm* — C. A. Whealy

(57) ABSTRACT

A new and distinct cultivar of *Chrysanthemum* plant named 'G19FON04YE', characterized by its upright, outwardly spreading and uniformly rounded plant habit; vigorous growth habit; freely branching habit; dense and full plant habit; dark green-colored leaves; uniform and freely flowering habit; long flowering period; and decorative-type inflorescences with ray florets that are bright yellow in color.

1 Drawing Sheet

Botanical designation: *Chrysanthemum* X *morifolium*.
Cultivar denomination: 'G19FON04YE'.

CROSS-REFERENCED TO CLOSELY-RELATED APPLICATIONS

Title: *Chrysanthemum* Plant Named 'G19FON01WH'
Applicant: Elien Sofie Pieters
Filed: Jan. 13, 2018 Ser. No. 15/732,924
Title: *Chrysanthemum* Plant Named 'G19FON11OR'
Applicant: Elien Sofie Pieters
Filed: Jan. 13, 2018 Ser. No. 15/732,912

BACKGROUND OF THE INVENTION

The present invention relates to a new and distinct cultivar of *Chrysanthemum* plant, botanically known as *Chrysanthemum* X *morifolium* and hereinafter referred to by the name 'G19FON04YE'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive ray floret coloration.

The new *Chrysanthemum* plant is a naturally-occurring whole plant mutation of *Chrysanthemum* X *morifolium* 'G19FON06PI', disclosed in U.S. Plant patent application Ser. No. 15/732,911. The new *Chrysanthemum* plant was discovered and selected by the Inventor as a single plant from within a population of plants of 'G19FON06PI' in a controlled greenhouse environment in Oostnieuwkerke, Belgium in October, 2016.

Asexual reproduction of the new *Chrysanthemum* plant by vegetative terminal cuttings was first conducted in a controlled greenhouse environment in Oostnieuwkerke, Belgium in January, 2017. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'G19FON04YE'. These characteristics in combination distinguish 'G19FON04YE' as a new and distinct *Chrysanthemum* plant:

1. Upright, outwardly spreading and uniformly rounded plant habit; vigorous growth habit.
2. Freely branching habit; dense and full plant habit.
3. Dark green-colored leaves.
4. Uniform and freely flowering habit.
5. Long flowering period.
6. Decorative-type inflorescences with ray florets that are bright yellow in color.

Plants of the new *Chrysanthemum* can be compared to plants of the mutation parent, 'G19FON06PI'. Plants of the new *Chrysanthemum* differ primarily from plants of 'G19FON06PI' in the following characteristics:

1. Plants of the new *Chrysanthemum* are more uniform than plants of 'G19FON06PI'.
2. Ray florets of plants of the new *Chrysanthemum* are bright yellow in color whereas ray florets of plants of 'G19FON06PI' are pink in color.

Plants of the new *Chrysanthemum* can be compared to plants of the *Chrysanthemum* X *morifolium* 'G19FON01WH', disclosed in U.S. Plant patent application Ser. No. 15/732,924. In side-by-side comparisons, plants of the new *Chrysanthemum* differ primarily from plants of 'G19FON01WH' in ray floret color as ray florets of plants of the new *Chrysanthemum* are bright yellow in color whereas ray florets of plants of 'G19FON01WH' are white in color.

Plants of the new *Chrysanthemum* can be compared to plants of the *Chrysanthemum* X *morifolium* 'G19FON11OR', disclosed in U.S. Plant patent application Ser. No. 15/732,912. In side-by-side comparisons, plants of the new *Chrysanthemum* differ primarily from plants of 'G19FON11OR' in ray floret color as ray florets of plants of the new *Chrysanthemum* are bright yellow in color whereas ray florets of plants of 'G19FON11OR' are greyed orange in color.

Plants of the new *Chrysanthemum* can also be compared to plants of *Chrysanthemum* X *morifolium* 'Amiko Yellow', disclosed in U.S. Plant Pat. No. 23,765. In side-by-side comparisons, plants of the new *Chrysanthemum* differ primarily from plants of 'Amiko Yellow' in the following characteristics:

1. Plants of the new *Chrysanthemum* are more uniformly rounded than plants of 'Amiko Yellow'.
2. Plants of the new *Chrysanthemum* flower about two to three weeks earlier than plants of 'Amiko Yellow'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. The photograph comprises a side perspective view of a typical flowering plant of 'G19FON04YE' grown in a container.

DETAILED BOTANICAL DESCRIPTION

The aforementioned photograph and following observations and measurements describe plants grown in 19-cm containers in an outdoor nursery in Oostnieuwkerke, Belgium during the summer and autumn and under cultural practices generally used in commercial *Chrysanthemum* production. During the production of the plants, day temperatures ranged from 20° C. to 25° C. and night temperatures ranged from 12° C. to 18° C. Plants were 20 weeks old when the photograph and detailed description were taken. In the following description, color references are made to The Royal Horticultural Society Colour Chart, 2007, Fifth Edition, except where general terms of ordinary dictionary significance are used.

Botanical classification: *Chrysanthemum* X *morifolium* 'G19FON04YE'.

Parentage: Naturally-occurring whole plant mutation of *Chrysanthemum* X *morifolium*, 'G19FON06PI', disclosed in U.S. Plant patent application Ser. No. 15/732,911, not patented.

PROPAGATION:

*Type cutting*.—By vegetative tip cuttings.

*Time to initiate roots, summer*.—About two weeks at temperatures about 20° C.

*Time to initiate roots, winter*.—About 20 days at temperatures about 20° C.

*Time to produce a rooted young plant, summer*.—About 30 days at temperatures about 20° C.

*Time to produce a rooted young plant, winter*.—About 40 days at temperatures about 20° C.

*Root description*.—Fine, fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Appearance*.—Perennial decorative-type *Chrysanthemum*; stems upright and outwardly spreading giving a uniformly rounded appearance to the plant; plants roughly spherical; very freely branching habit, about 20 primary lateral branches develop, each primary lateral branch with multiple secondary branches; pinching enhances lateral branch development; dense and full plant habit; vigorous growth habit; plants flexible, not brittle.

*Plant height*.—About 45 cm.

*Plant width*.—About 60 cm.

*Lateral branches*.—Length: About 30 cm. Diameter: About 2 mm to 3 mm. Internode length: About 3 cm. Strength: Moderately strong, flexible. Texture: Pubescent, fine; longitudinally ridged. Color: Close to 141A.

*Leaves*.—Arrangement: Alternate, simple. Length: About 4.5 cm to 6 cm. Width: About 2.5 cm to 3 cm. Apex: Rounded. Base: Attenuate. Margin: Palmately lobed and serrate, sinuses between lateral lobes divergent to parallel. Texture, upper and lower surfaces: Slightly pubescent. Venation: Palmately reticulate. Color: Developing leaves, upper surface: Close to 141A. Developing leaves, lower surface: Close to 139C. Fully expanded leaves, upper surface: Close to 137A; venation, close to 148C. Fully expanded leaves, lower surface: Close to 137C; venation, close to 147B to 147C. Petioles: Length: About 1 cm. Diameter: About 2 mm. Texture, upper and lower surfaces: Slightly pubescent; slightly rough. Color, upper surface: Close to 137A. Color, lower surface: Close to 137C. Stipules: Length: About 1 cm. Diameter: About 2 mm. Texture, upper and lower surfaces: Slightly pubescent; rough. Color, upper and lower surfaces: Close to 137A.

Inflorescence description:

*Appearance*.—Decorative-type inflorescence form; inflorescences borne on terminals above foliar plane; disc and ray florets arranged acropetally on a capitulum.

*Fragrance*.—Slightly fragrant, pungent.

*Flowering response*.—Under natural season conditions, plants flower in early September in Belgium; flowering response time, about 32 days.

*Postproduction longevity*.—Inflorescences maintain good color and substance for about 38 to 40 days in an outdoor nursery; inflorescences persistent.

*Quantity of inflorescences*.—About 20 to 25 inflorescences develop per lateral branch.

*Inflorescence buds*.—Height: About 6 mm. Diameter: About 8 mm. Shape: Globular. Color: Close to 12A.

*Inflorescence diameter*.—About 6 cm.

*Inflorescence depth (height)*.—About 3.5 cm.

*Disc diameter*.—About 7 mm; inconspicuous.

*Receptacle diameter*.—About 3 mm.

*Receptacle height*.—About 2.5 mm to 3 mm.

*Receptacle color*.—Close to 144B.

*Ray florets*.—Length: About 3.5 cm to 5 cm. Width: About 7 mm. Shape: Oval. Apex: Rounded. Base: Attenuate. Margin: Entire. Aspect: Mostly flat. Texture and luster, upper and lower surfaces: Smooth, glabrous; matte. Number of ray florets per inflorescence: About 125 to 150 arranged in about seven whorls. Color: When opening, upper surface: Close to 12A. When opening, lower surface: Close to 7D. Fully opened, upper surface: Close to 7A; proximally, close to 12A; color becoming closer to 7D development. Fully opened, lower surface: Close to 7D; color does not change with development.

*Disc florets*.—Length: About 3 mm. Diameter: About 0.5 mm to 1 mm. Shape: Tubular; apices acute. Number of disc florets per inflorescence: About 60 to 80 massed at the center of the inflorescence. Texture and luster: Smooth, glabrous; glossy. Color, immature: Close to 145A. Color, mature: Close to 12A.

*Phyllaries*.—Number of phyllaries per inflorescence: About 25 arranged in two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Color, upper surface: Close to 137A. Color, lower surface: Close to N137B.

*Peduncles*.—Length, terminal peduncle: About 5 cm. Length, fourth peduncle: About 7 cm. Length, seventh peduncle: About 7 cm. Diameter: About 2.5 mm. Angle: About 30° from vertical. Strength: Strong. Texture: Slightly pubescent. Color: Close to 146B.

*Reproductive organs*.—Androecium: Not observed. Gynoecium: Not observed.

*Seeds and fruits*.—To date seed and fruit production have not been observed on plants of the new *Chrysanthemum*.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'G19FON04YE' as illustrated and described.

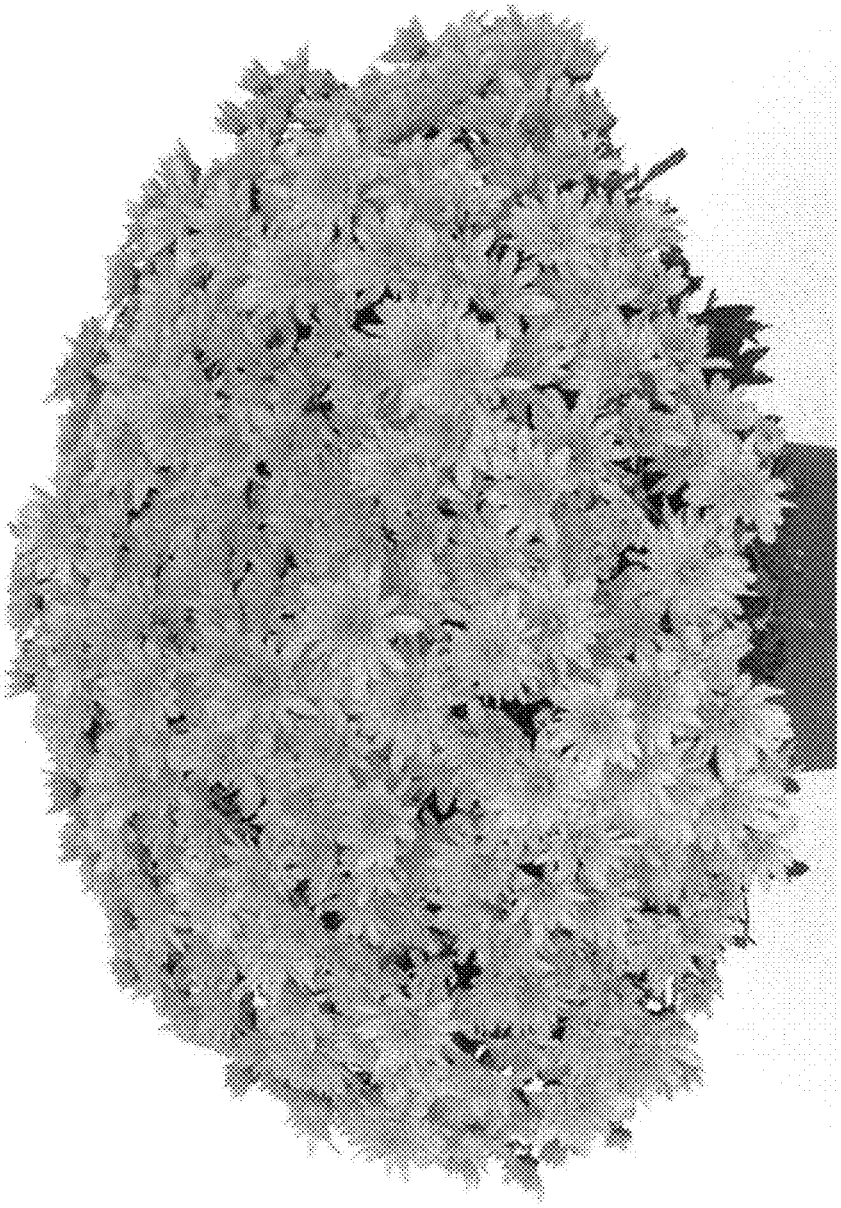

* * * * *